US006475537B1

(12) United States Patent
King et al.

(10) Patent No.: US 6,475,537 B1
(45) Date of Patent: Nov. 5, 2002

(54) HOPS ACID ANTIBACTERIAL COMPOSITIONS

(75) Inventors: William King, Walnut Creek, CA (US); Xintian Ming, Cottage Grove, WI (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 09/626,851

(22) Filed: Jul. 27, 2000

(51) Int. Cl.$^7$ ................................................ A61K 35/78
(52) U.S. Cl. .................. 424/778; 424/773; 424/774; 424/776; 424/779; 424/725; 424/405
(58) Field of Search ................... 426/271; 424/725, 424/404, 405, 439, 750, 774, 778; 435/410

(56) References Cited

U.S. PATENT DOCUMENTS

| 3,932,603 A |   | 1/1976  | Haas             |
| 4,170,638 A |   | 10/1979 | Owades           |
| 4,401,684 A | * | 8/1983  | Versluys         |
| 5,082,975 A | * | 1/1992  | Todd, Jr. et al. |
| 5,166,449 A |   | 11/1992 | Todd, Jr. et al. |
| 5,286,506 A |   | 2/1994  | Millis et al.    |
| 5,370,863 A |   | 12/1994 | Barney et al.    |
| 5,455,038 A |   | 10/1995 | Barney et al.    |
| 5,578,307 A |   | 11/1996 | Wunderlich et al.|
| 5,968,539 A |   | 10/1999 | Beerse et al.    |
| 6,106,851 A |   | 8/2000  | Beerse et al.    |
| 6,113,933 A |   | 9/2000  | Beerse et al.    |
| 6,129,907 A |   | 10/2000 | Sreenivasan et al.|

FOREIGN PATENT DOCUMENTS

| JP | 06098738    |   | 4/1994  |
| JP | 07196572    |   | 8/1995  |
| KR | 9411072 B1  | * | 11/1994 |
| WO | WO 9733971  |   | 9/1997  |
| WO | WO 9908547  |   | 2/1999  |

OTHER PUBLICATIONS

Shelef et al., "Antibacterial Effects of Butylated Hydroxyanisole (BHA) against Bacillus species", Journal of Food Science, 1982, 47(3), p. 796–799.*

The Merck Index, Tenth Edition, 1983.*

* cited by examiner

*Primary Examiner*—Leon B. Lankford, Jr.
*Assistant Examiner*—Ruth A. Davis
(74) *Attorney, Agent, or Firm*—Dilworth & Barrese, LLP

(57) ABSTRACT

An antibacterial composition of matter comprising: (a) one or more hops acid or hops acid derivatives or hops resin or hops resin derivatives; and (b) one or more food grade surfactants, surface active agents, chelating agents, antioxidants, and/or organic acids is provided.

4 Claims, No Drawings

HOPS ACID ANTIBACTERIAL COMPOSITIONS

FIELD OF THE INVENTION

The present invention relates to a process for reducing the level or retarding the outgrowth of bacteria on food and nonfood products by treatment with a composition which includes one or more safe and suitable hops acids or hops acid derivatives or hops resins or hops resin derivatives and one or more surfactants, surface active agents, chelators, antioxidants and/or organic acids. More specifically, the process comprises using as an ingredient or applying to a food surface or a nonfood product a composition comprising beta hops acids and one or more nonionic surfactants, chelators, antioxidants and/or organic acids in order to reduce or eliminate gram positive spoilage or pathogenic bacteria, and especially strains of the harmful pathogen *Listeria monocytogenes*.

BACKGROUND OF THE INVENTION

Extensive research has been conducted in the field of food and consumer care products safety to develop compositions which function as food grade anti-bacterials. In particular, gram positive bacteria such as *Listeria monocytogenes, Staphlococcus aureus, Bacillus cereus, Clostridium botulinum* and the like, when found in foods or consumer care products may pose significant health risks to users. Further, miscellaneous gram positive spoilage bacteria such as *lactobacilli, bacilli*, streptomyces, and micrococci species may cause reduction in the shelf life and appeal of processed foods and high moisture consumer care products. Both pathogenic and spoilage bacteria occur most commonly at the surfaces of foods or consumer care ingredients, which come into contact with undesirable bacteria by contamination from environmental sources. These bacteria then spread to other parts of the food through mixing, comminuting, wetting action, or migration. The bacteria may then grow during handling and storage of the product, resulting in either spoilage or infectious health risks. Use of such products in sensitive body openings, such as the mouth, the skin, the eyes, or ingestion of food products profoundly increases the chance of contracting infection. In addition, other gram positive bacteria including the miscellaneous spoilage species, can opportunistically infect open cuts and wounds that are treated with consumer products normally meant for external use only. The growth of all bacteria during handling and distribution must therefore be meticulously prevented and minimized in all foods and consumer care products. This invention discloses one such system for the reduction and inactivation of bacteria in food and consumer care products that are at risk.

U.S. Pat. Nos. 5,286,506 and 5,455,038 suggest that acid or acid derivatives from hops (used in beer manufacture) may have antibacterial activity against Listeria species. However, Johnson et al disclose in the International Journal of Food Microbiology 33 (1996) 195–207 that hops acid preparations and hops acid derivatives have limited practical efficacy against bacteria in fat containing products such as cheeses, meats, sauces, and dressings. This is presumably due to the migration or entrapment of the beta acids in the fat emulsion and their subsequent unavailability for inhibition of bacterial growth in the aqueous portion of the emulsion where bacteria are known to grow. This problem of poor activity of hops beta acids in fatty acid containing foods has prevented them from being used commercially as natural anti-microbial agents for control of listeria or other gram positive pathogens. Further, it is unlikely that hops acid activity would prove effective in the water in oil emulsions common among most consumer care products. The ability to tag the hops acids in the aqueous phase of such systems is a property that would dramatically increase their value as anti-microbials in either food or consumer care products containing high oil or fatty acid levels.

To the extent necessary for completion of this patent application, all of the cited references are expressly incorporated by reference. However, despite the above teachings, there still exists a need in the art for a method for protecting fat containing foods and consumer care products against bacterial growth using natural, generally recognized as safe (GRAS) substances. More specifically, there exists a need for more complete and effective reduction of harmful pathogens by use of safe and suitable levels of food grade anti-microbial ingredients such as hops acids whereby the hops acids may be distributed effectively to the aqueous phase of the products to be treated.

BRIEF SUMMARY OF THE INVENTION

It is now discovered, quite surprisingly, that a composition which has as a first component, at least one compound selected from the group consisting of hops acids, hops acid derivatives, hops resins, and hops resin derivatives; and as a second component, at least one compound selected from the group consisting of food grade surfactants, surface active agents, chelators, antioxidants, and organic acids provides excellent antibacterial properties, especially against potentially harmful gram positive bacteria of the Listeria genus and can easily be applied to the foods or consumer products based on oil in water emulsions.

One embodiment of the present invention comprises an antibacterial composition comprising: (a) a first component having at least one compound selected from the group consisting of hops acids, hops acid derivatives, hops resins, and hops resin derivatives; and (b) a second component having at least one compound selected from the group consisting of food grade surfactants and surface active agents. Particularly preferred is a composition containing beta hops acids and a food grade surfactant or surface agent which is either a nonionic surfactant, a propylene glycol, or a mixture thereof.

In another embodiment, the present invention provides a method for reducing, retarding, or even eliminating gram positive bacteria, and especially the *Listeria monocytogenes*, in food products comprising the step of treating the surfaces of said food product with a bacteristatically or bactericidally effective amount of a composition comprising: (a) a first component having at least one compound selected from the group consisting of hops acids, hops acid derivatives, hops resins, and hops resin derivatives; and (b) one or more food grade surfactants and/or surface active agents.

It is an object of the present invention to provide a process for treating food products in order to protect against harmful bacteria.

An additional object of the present invention is to provide a novel composition having substantially greater antibacterial properties than previously observed for the individual components of the composition.

An additional object of the present invention is to provide a product which is easily applied to all surfaces of a food product which is potentially susceptible to bacterial degradation.

A final object of the present invention is to provide a product which can work well under the partitioning conditions of a fat or oil in water emulsion.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention provides a novel antibacterial composition and its use in a process for reducing, retarding, or totally eliminating harmful bacteria, preferably from food surfaces.

The novel antibacterial composition comprises: (a) one or more hops acids or hops acid derivatives or hops resins or hops resin derivatives or mixtures thereof; and (b) one or more food grade surfactants or surface active agents or chelators, or antioxidants, or organic acids, or mixtures thereof, preferably food grade surfactants or surface active agents or mixtures thereof.

The first component of the novel composition is one or more hops acids, or hops acid derivatives, or hops resins, or hops resin derivatives, or mixtures thereof. The bitter acids component of the hops used in beer making and particularly the beta-acids have now been found to be useful as bactericides in food products. The most prevalent groups of bitter acids found as components of hops are the alpha-acids and the beta-acids, also referred to as humulones and lupulones, respectively. Both contribute bitterness to beer, but the alpha-acids are much more intense in this regard than the beta-acids. Producers of hop extracts isolate the alpha and beta acids commercially by various chromatographic techniques and have recently developed a technique to separate the two acid fractions using liquid carbon dioxide under supercritical conditions. A by-product of the operation is a product which contains approximately 61 weight percent beta-acids, the remainder consisting essentially of hops resins. This by-product can be standardized with maltodextrin or other food grade carrier, spray-dried, and used as an antibacterial food ingredient. A referred beta hops acids component is commercially available as a natural flavor extract containing 1 weight percent beta hops acids.

The alpha-acids contained in hops are commonly known as humulone, cohumulone and adhumulone, while the beta-acids contained in hops are commonly known as lupulone, colupulone and adlupulone. Derivatives of the hops acids or hops resins which have demonstrated antibacterial properties such as hexahydrocolupulone and tetrahydroisohumulone, as disclosed in U.S. Pat. No. 5,455,038, are specifically contemplated for use in association with the present invention. Also considered as specifically contemplated for use in association with the present invention is the use of the acid salt forms of the hops acids or hops resins.

In practice, the hop acid or resin or derivative thereof is added to the food product in amounts between about 0.1 to about 50 ppm (by weight of solution used for treatment), more preferably between about 0.40 to about 20 ppm.

The preferred second component of the novel composition comprises one or more food grade surfactants or surface active agents. The term "surface active agent" is intended to also include what is commonly known as a protective colloid.

The surfactant employed preferably is a food grade emulsifier with a high hydrophilic/lipophilic balance (HLB) value. Such values should range from about 10 to about 16. Suitable emulsifiers preferably have also been approved for use in foods since many of the applications for the present invention reside in the food and drug industries. Preferably, the emulsifier is selected from the group consisting of polyoxyethylene sorbitan esters, sorbitan esters, monoglycerides, diglycerides, lecithin, polyglycerols, sodium stearoyl-2-lactylate, stearyl-2-lactylic acid, polyoxystearates, acetylated monoglycerides and mixtures thereof. Preferably, sorbitan esters and polyoxyethylene sorbitan esters are the emulsifiers of choice. The above list is considered only a representative listing as the present invention contemplates the use of any food grade surfactant.

Particularly preferred commercially available surfactants include: Tween-80, a trademark of ICI Americas Inc. for polyoxyethylene sorbitol ester; Tween-20, a trademark of ICI Americas Inc. for polyoxyethylenesorbitan monolaurate; and Triton X-100, a trademark of Union Carbide Chemicals and Plastics Co. Inc. for octylphenol ethylene oxide condensate.

When a surfactant is used in combination with the hops acids or resins or hops acid or resin derivatives, it is added in an amount ranging from about 0.1 to 10%, more preferably between 0.5 to 5% of the treatment composition.

Alternatively, a food grade surface active agent other than a surfactant can be selected. This includes, but is not limited to polyhydric alcohols such as polyethylene glycols, more specifically polypropylene glycol, and other compounds having multiple hydroxy groups such as, glycerol, sorbitol, mannitol, inositol, and the like. Protective colloids such as polyvinyl alcohol are also specifically considered for use in accordance herewith.

When a surface active agent other than a surfactant is used in combination with the hops acids or hops acid derivatives, it is added in an amount ranging from about 0.1 to 20%, more preferably between 0.5 to 10% of the treatment composition.

The combination of hops acids or hops acid derivatives with both a surfactant and a surface active agent other than a surfactant is also specifically contemplated as falling within the scope of the present invention.

The second component of the compositions of this invention can comprise a chelating agent; preferably one selected from the group consisting of citrates, disodium ethylenediaminetetraacetate ($Na_2$ EDTA), dicalcium ethylenediaminetetraacetate (CaEDTA), ethylene glycol-bis(beta-aminoethyl ether)-tetraacetic acid (EGTA), and mixtures thereof. Most preferably, the chelating agent comprises sodium citrate.

Alternatively, the second component of the compositions of this invention can comprise an antioxidant; preferably one selected from the group consisting of butylated hydroxyanisole, butylated hydroxytoluene, monotertbutylhydroquinone (TBHQ), propylgallate ascorbic acid, tocopherols, and mixtures thereof. Most preferably, the antioxidant comprises butylated hydroxyanisole.

Also, the second component of the compositions of this invention can comprise an organic acid; preferably one selected from the group consisting of acetic acid, lactic acid, propionic acid, benzoic acid, sorbic acid, and their salts.

Other additives which can be present in the inventive composition include, but are not limited to the following materials: other antibacterial agents, natural or synthetic seasonings, oils, and/or flavors, dyes and/or colorants, vitamins, minerals, nutrients, enzymes, binding agents such as guar gum and xanthan gum and the like. The addition of these materials is not considered critical to the success of the present invention and this addition would be considered to be within the skill of the artisan.

The antimicrobial composition of the present invention may be used in connection with any food or high moisture consumer care product that is susceptible to bacterial growth or degradation. Typical food products include, but are not limited to fruits and vegetables including derived products, grain and grain derived products, dairy foods, cooked meats, poultry, and seafood. In particularly preferred embodiments, the composition is used in connection with meat, poultry and/or seafood, home meal replacements, soups, deli salads, processed cheese, tofu, beverages, or other ready to eat food products. Typical consumer care applications include, but are not limited to moisture containing cosmetics, oral care products, skin care products, hair care products, eye care products, feminine hygiene products, liquid soaps, shampoos, and detergents.

To selectively reduce the level of gram positive bacteria on a food surface, the novel composition may be applied to the food surface. In practice the application of the composition of matter to the food surface may either be a direct application or an indirect application such as by first coating a packaging material or casing and subsequently bringing the packaging material or casing into intimate contact with the food surface. The use of the term "food surface" is defined to include any and all internal or external surfaces of the food product being treated.

The composition according to the present invention is most readily used by mixing along with the other ingredients in a blended food or consumer care product, but should also be effective to treat the surface of solid food products by a rinse, spray, packaging material, or by application to the interior of such products, e.g., by injection. In still other embodiments, the composition may be applied as a marinate, breading, seasoning rub, glaze, colorant mixture, and the like, the key criteria being that the antimicrobial composition be available to the surface subject to bacterial degradation. In still other embodiments, the composition may be indirectly placed into contact with the food surface by applying the composition to food packaging and thereafter applying the packaging to the food surface. The optimum amount to be used will depend on the composition of the particular food product to be treated and the method used for applying the composition to the food surface, but can be determined by simple experimentation.

The compositions of this invention are effective against gram positive bacteria including, but not limited to the following bacteria: Listeria bacteria such as *Listeria monocytogenes*, Staphylococcus bacteria such as *Staphylococcus aureus*, Clostridia bacteria, Bacillus bacteria, micrococci, streptococci, or other lactic acid bacteria. Under certain conditions, use of the inventive composition reduces bacterial levels to levels undetectable by standard enrichment techniques.

The invention will be further described by the following non-limiting examples.

EXAMPLE 1

Activity of Beta Hop Acid (BHA) and a Non-ionic Surfactant Against *Listeria monocytogenes*

As shown in Table 1, two groups of tests are conducted in Trypticase soy broth, pH 6.0 at 30° C. for 48 hours to show the effect of a bactericidal system containing BHA and the surfactant Tween-80 (polyoxyethylene sorbitol ester). The test of BHA without Tween-80 serves as the control to show the effect of BHA alone against *L. monocytogenes*. The test of BHA with Tween-80 demonstrates a surprisingly enhanced bactericidal activity of this composition against *L. monocytogenes*. Table 1 shows that at a concentration of 0.125 ppm BHA and 2% Tween-80, the bactericidal system has a 3 log reduction of the target bacteria, while less then 1 log deduction is observed at the same concentration of BHA without Tween-80. At higher concentrations of BHA, the BHA and Tween-80 combination virtually eliminates the bacteria levels to less than 10/ml. Thus, the composition of BHA and Tween-80 demonstrate a synergistic activity of greater then 20 times that of BHA alone.

TABLE 1

| BHA preparation * | CFU/ml | |
| --- | --- | --- |
| ppm | with 2% Tween-80 | without Tween-80 |
| 0 | 2.2 × 10e8 | 2.1 × 10e8 |
| 250 (0.125) | 1.5 × 10e4 | 3.3 × 10e7 |
| 500 (0.25) | 20 | 5.4 × 10e6 |
| 1000 (0.5) | <10 | 4.6 × 10e6 |
| 5000 (2.5) | <10 | 1.7 × 10e6 |

* BHA used is a raw extract preparation that contains about 5000 ppm pure beta hop acids.

EXAMPLE 2

Activity of BHA and a Water Activity Reducing Agent Against *Listeria monocytogenes*

As shown in Table 2, two groups of tests are conducted in Trypticase soy broth, pH 6.0 at 30° C. for 48 hours to show the effect of the bactericidal system containing BHA and propylene glycol, a water activity reducing agent. The test of BHA without propylene glycol served as the control to show the effect of BHA alone against *L. monocytogenes*. The test of BHA with propylene glycol demonstrates surprisingly enhanced bactericidal activity of the composition against *L. monocytogenes*. Table 2 shows that at a concentration of 0.125 ppm BHA and 8% propylene glycol, the bactericidal system causes a 2.5 log reduction in the target bacteria, while less then 1 log reduction is observed at the same concentration of BHA without propylene glycol. At higher concentrations of BHA, the BHA and propylene glycol combination virtually eliminate the bacteria, i.e., the combination reduces the levels to less than 10/ml. Thus, the composition of BHA and propylene glycol demonstrates a synergistic activity enhancement of greater then 20 times that of BHA alone.

TABLE 2

| BHA preparation * | CFU/ml | |
| --- | --- | --- |
| ppm | with 8% propylene glycol (PG) | without PG |
| 0 | 2.2 × 10e8 | 2.1 × 10e8 |
| 250 (0.125) | 7.8 × 10e5 | 3.3 × 10e7 |
| 500 (0.25) | 8.1 × 10e4 | 5.4 × 10e6 |
| 1000 (0.5) | 1000 | 4.6 × 10e6 |
| 5000 (2.5) | <10 | 1.7 × 10e6 |

* BHA used is a raw extract preparation that contains about 5000 ppm pure beta hop acids.

EXAMPLE 3

Synergism of Beta Hop Acid (BHA) and a Chelating Agent Against *Listeria monocytogenes*

As shown in Table 3, two groups of tests are conducted in trypticase soy broth, pH 6.0 at 30° C. for 48 hours to show the effect of a bactericidal system containing BHA preparation and a chelating agent, sodium citrate. The test of BHA without citrate serves as the control to show the effect of BHA alone against L. monocytogenes. The test of BHA with chelating agent demonstrates a surprising enhanced bactericidal activity of this composition against L. monocytogenes. Table 1 shows that at a concentration of 50 ppm BHA preparation and 0.5% sodium citrate, the bactericidal system has a 6 log reduction against the target bacteria, while less then 4 log reduction is observed at the same concentration of BHA preparation. Thus, the composition of BHA preparation and a chelating agent demonstrate a synergistic effect against L. monocytogenes.

TABLE 3

| BHA preparation * | CFU/ml | |
|---|---|---|
| | with 0.5% NaCitrate | without NaCitrate |
| 0 | 2.0 × 10e8 | 2.1 × 10e8 |
| 50 ppm | 40 | 6 × 10e4 |

* beta hop add preparation contains about 0.97% pure beta hop acids.

EXAMPLE 4

Synergism of Beta Hop Acid (BHA) and Antioxidant Against Listeria monocytogenes

As shown in Table 4, two groups of tests are conducted in Trypticase soy broth, pH 6.0 at 30° C. for 48 hours to show the effect of the bactericidal system containing BHA preparation and butylated hydroxyanisole, an antioxidant. The test of BHA without antioxidant served as the control to show the effect of BHA alone against L. monocytogenes. The test of BHA preparation with butylated hydroxyanisole demonstrates surprisingly enhanced bactericidal activity of the composition against L. monocytogenes. Table 2 shows that at a concentration of 50 ppm BHA preparation and 100 ppm butylated hydroxyanisole, the bactericidal composition causes a 6 log reduction in the target bacteria, while less then 4 log reduction is observed at the same concentration of BHA preparation without butylated hydroxyanisole. Thus, the composition of BHA preparation and an antioxidant demonstrates a synergistic effect against L. monocytogenes.

TABLE 4

| BHA preparation * | CFU/ml | |
|---|---|---|
| | with 100 ppm butylated hydroxyanisole | without butylated hydroxyanisole |
| 0 | 1.2 × 10e8 | 2.1 × 10e8 |
| 50 ppm | 50 | 6 × 10e4 |

* beta hop acid preparation contains about 0.97% pure beta hop acids.

EXAMPLE 5

Synergism of Beta Hop Acid (BHA) and Organic Acids Against Listeria monocytogenes As shown in Table 5, two groups of tests are conducted in Trypticase soy broth, pH 6.0 at 30° C. for 48 hours to show the effect of the bactericidal composition containing BHA preparation and organic acids t acetic acid, propionic acid and lactic acids. The test of BHA preparation served as the control to the synergistic effect against L. monocytogenes. The test of BHA preparation with organic acids demonstrates enhanced bactericidal activity of the composition against L. monocytogenes. Table 3 shows that at a concentration of 50 ppm BHA preparation and 500 ppm organic acids, the bactericidal composition causes a 3 log reduction in the target bacteria, while less then 4 log reduction is observed at the same concentration of BHA preparation when used alone. Thus, the composition of BHA preparation and an organic acid demonstrates a synergistic effect against L. monocytogenes.

TABLE 5

| BHA preparation * | CFU/ml | | | |
|---|---|---|---|---|
| | with 500 ppm organic acid | | | without |
| | acetic | propionic | lactic | organic acids |
| 0 | 1.2 × 10e8 | 1.4 × 10e8 | 2.0 × 10e8 | 2.1 × 10e8 |
| 50 ppm | 1.5 × 10e3 | 2.0 × 10e3 | 4.2 × 10e3 | 6 × 10e4 |

* beta hop acid preparation contains about 0.97% pure beta hop acids.

Having described the invention in detail and by reference to the preferred embodiments thereof, it will be apparent that modifications and variations are possible without departing from the scope of the appended claims.

What is claimed is:

1. An antibacterial composition of matter comprising: (a) a first component including at least one compound selected from the group consisting of hops acids and hops acid derivatives; and (b) a chelating agent comprising disodium ethylenediaminetetraacetate ($Na_2$ EDTA).

2. The composition according to claim 1 wherein the first component comprises 0.1 to 500 ppm by weight of the composition.

3. The composition according to claim 1 wherein said chelating agent comprises 0.01 to 5% by weight of the composition.

4. The composition according to claim 1 wherein said chelating agent comprises 0.1 to 1% by weight of the composition.

* * * * *